(12) United States Patent
Gritsus et al.

(10) Patent No.: US 6,250,306 B1
(45) Date of Patent: Jun. 26, 2001

(54) ASSESSMENT OF ISCHEMIC WOUND HEALING THERAPEUTICS

(75) Inventors: Vadim Gritsus, Morristown; Maria Cristina Niciporciukas, Long Valley; Laura Iarkowski, Belle Mead; James Ward, Stewartsville, all of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/248,668

(22) Filed: Feb. 11, 1999

Related U.S. Application Data
(60) Provisional application No. 60/074,641, filed on Feb. 13, 1998.

(51) Int. Cl.$^7$ ............................ A61B 17/00; G09B 23/28; A61F 2/10

(52) U.S. Cl. ............................ 128/898; 623/1.15; 623/8; 600/32; 434/262

(58) Field of Search ........................... 128/898; 623/1.15; 623/8; 434/262; 600/32

(56) References Cited

U.S. PATENT DOCUMENTS

| | | | |
|---|---|---|---|
| 4,828,560 | * | 5/1989 | Heyler, III ............................... 623/8 |
| 5,382,514 | | 1/1995 | Passaniti et al. . |

OTHER PUBLICATIONS

Medline Database, Abstract No. XP–002131852.
Medline Database, Abstract No. XP–002131853.
Boggett D., et al., "Laser Doppler Measurements of Blood Flow in Skin Tissue", *J. Biomed. Eng.*, vol. 7, Jul. 1985.
Brown, David M., et al. "Platelet–derived growth factor BB induces functional vascular anastomoses in vivo", *Proc. Natl. Acad. Sci. USA*, vol. 92, pp. 5920–5924, Jun. 1995.
Cooley, Brian C., et al. "The Influence of Diabetes on Free Flap Transfer: II. The Effect of Ischemia on Flap Survival", *Annals. of Plastic Surgery*, vol. 29, No. 1, Jul. 1992.
Fagrell, Bengt, "Microcirculatory Methods For The Clinical Assessment of Hypertension, Hypotension, and Ischemia", *Annals of Biomedical Engineering*, vol. 14, pp. 163–173 (1986).
Franken, Ralph, "Non–Revascularized Epigastric Free Flap: No All–Or–None Survival Pattern", *Microsurgery*, 14:579–583 (1993).
Fukui, Akihiro, et al. "Venous Flap–Its Classification and Clinical Applications", *Microsurgery*, 15:571–578 (1994).
Hallock, Geoffrey G., "Preexpansion of Free Flap Donor Sites Used in Reconstruction after Burn Injury", *Journal of Burn Care & Rehabilitation*, vol. 16, No. 6, pp. 646–653 (1995).
Hammond, Dennis C., et al. "The Dorsal Skin–Flap Model in the Rat: Factors Influencing Survival", *Plastic and Reconstructive Surgery*, pp. 316–321, Feb. 1993.

Hammond, Dennis C., et al. "The Effect of Occlusion on the Survival of an Isolated Dorsal Skin Flap in the Rat", *Annals. of Plastic Surgery*, vol. 29, No. 3, Sep. 1992.
Holloway, G., et al., "Laser Doppler Measurement of Cutaneous Blood Flow", *The Journal of Investigative Dermatology*, 69:306–309 (1977).
Itoh, Y., "An Experimental Study of Prefabricated Flaps Using Silicone Sheets, with Reference to the Vascular Patternization Process", *Annals. of Plastic Surgery*, vol. 28, No. 2, Feb. 1992.
Johnson, T., et al. "Histology and Physiology of Tissue Expansion", *J. Dermatol. Surg. Oncol.*, vol. 19, pp. 1074–1078 (1993).
Larrabee, W., et al. "Wound Tension and Blood Flow in Skin Flaps", *Ann. Otol. Rhinol. Laryngol.*, vol. 93, pp. 112–115, 1984.
LeGrand, E., "Comparison of Pig and Guinea Pig Full and Partial Thickness Skin Excision Wound Models for Evaluating the Effects of rhPDGF–BB", *Wounds*, vol. 7, No. 3, May/Jun. 1995.
Lenoble, G., et al. "Observations on Experimental Flow–through Venous Flaps", *British Journal of Plastic Surgery*, vol. 46, pp. 378–383 (1993).
Marzella, L., et al. "Regional Hemodynamics in 1–Day–Delayed Rodent Island Flaps", *Journal of Surgical Research*, vol. 56, pp. 466–472 (1994).
Mast, B., et al. "Interactions of Cytokines, Growth Factors, and Proteases in Acute and Chronic Wounds", *Wound Rep. Reg.*, vol. 4, pp. 411–420 (1996).
McFarlane, R.M., et al. "A Study of the Delay Phenomenon in Experimental Pedicle Flaps", *Plastic and Reconstructive Surgery*, vol. 35, No. 3, pp. 245–262 (1965).
Nieto, S., et al. "A Comparative Study on the Effect of Various Pharmacological Agents on the Survival of Skin Flaps in the Rat", *British Journal of Plastic Surgery*, vol. 45, pp. 113–116 (1992).
Nilsson, G., et al. "Laser Doppler Flowmetry–A New Technique for Nonivasive Assessment of Skin Blood Flow", *Cosmetics & Toiletries*, vol. 99, pp. 97–108, Mar. 1984.
Nishikawa, H., et al. "Ultrastructural Changes in Rat Adipomusculocutaneous Flaps During Warm Ischaemic Storage and Reperfusion", *Int. J. Exp. Path*, vol. 74, pp. 45–53 (1993).
Oberg, P., et al. "Laser–Doppler Flowmetry", *Biomedical Engineering*, vol. 18, Issue 2, pp. 125–163 (1990).

(List continued on next page.)

*Primary Examiner*—David J. Isabella
*Assistant Examiner*—Choon P. Koh
(74) *Attorney, Agent, or Firm*—Scully, Scott, Murphy & Presser

(57) ABSTRACT

The present invention is directed to the assessment of ischemic wound therapeutics by characterizing wound healing parameters such as epithelialization, granulation tissue formation and contraction. The present invention is also directed to an animal model for assessing ischemic wound therapeutics.

15 Claims, 15 Drawing Sheets

(2 of 15 Drawing Sheet(s) Filed in Color)

OTHER PUBLICATIONS

Odland, R., et al. "Nonsurgical Delay of Skin Flaps: Effect of a Suture Delay Technique on Blood Flow and Survival", *Laryngoscope,* vol. 105, pp. 523–528, May 1995.

Pittet, B., et al. "The Role of Neovascularization in the Survival of an Arterialized Venous Flap", *Plastic and Reconstructive Surgery,* pp. 621–629, Mar. 1996.

Powers, E., et al. "Laser Doppler Measurement of Blood Flow in the Microcirculation", *Plastic and Reconstructive Surgery,* vol. 16, No. 2, pp. 250–255 (1978).

Quirinia, A., et al. "Ischemia in Wound Healing I: Design of a Flap Model–Changes in Blood Flow", *Scand. J. Plast. Reconstr. Hand Surg.,* vol. 26, pp. 21–28 (1992).

Schwartz, D., et al. "Altered Collagen Metabolism and Delayed Healing in a Novel Model of Ischemic Wounds", *Wound Repair and Regeneration,* vol. 3, No. 2, pp. 204–212.

Wysocki, A., "Wound Measurement", *International Journal of Dermatology* vol. 35, No. 2, Feb. 1996.

* cited by examiner

ASSESSMENT OF ISCHEMIC WOUND HEALING THERAPEUTICS

This application claims priority from U.S. Provisional Application No. 60/074,641, filed Feb. 13, 1998.

FIELD OF THE INVENTION

The present invention is directed to the assessment of ischemic wound therapeutics by characterizing wound healing parameters such as epithelialization, granulation tissue formation and contraction. The present invention is also directed to an animal model for assessing ischemic wound therapeutics.

BACKGROUND OF THE INVENTION

Tissue ischemia is a condition resulting from hypoperfusion which is caused by arterial occlusion, veneous obstruction or impaired microcirculation. Ischemia predisposes individuals to the development of chronic wounds. Chronic ischemic conditions impair the normal wound healing process in the tissue affected. Many components of the normal wound healing process such as epithelialization, contraction and granulation tissue formation are inhibited as a direct result of perfusion disturbances.

Numerous studies have been undertaken in an effort to develop a model of cutaneous ischemia for use in assessing the efficacy of wound healing therapeutics. However, many investigators report that conditions of chronic tissue ischemia are difficult to create in animal models. Several factors alone or in combination render current methods and models unacceptable for tissue ischemia research. For example, surgical creation of a cutaneous flap on an animal results in an abrupt reduction of blood flow through the flap, which is not characteristic of the chronic ischemia. Furthermore, rapid revascularization of the flap from contact with underlying tissue renders the flap non-ischemic. Moreover, prior art ischemia models are prone to infection, drying and necrosis because they lack a closed structure.

Schwartz, et al. employed an ischemia bipedicle flap rat model (1995) *Wound Repair and Regeneration* 3:204–212. The bipedicle flap was prepared by making two longitudinal incisions on both sides of the spine. The flap, thus created was bluntly lifted and then sutured back to the animal. Subsequently, wounds were made in the flap. However, the flap rapidly revascularized, causing a cessation of ischemia.

Pittet, et al. (1996) *Plast. Reconstr. Surg.* 97:621–629 prepared an "H-shaped" flap model. Two parallel incisions (one on each side of the rats spine). The flap was subsequently separated from the underlying tissue followed by a transverse full thickness incision in the center of the flap. The flap was separated into two pieces, cranial and caudal, resembling an "H" structure. The transverse incision was immediately closed and the flap was sutured back to the underlying structures. Wounds were created in the flap on both sides of the transverse incision. This model suffers from unpredictable reproducibility of the healing process of the wounds due to necrosis and/or revascularization of the flap.

McFarlane, et al. (1965) *Reconstructive Surgery* 35(3):245–262 prepared a monopedicle flap on the back of rats. Two parallel longitudinal incisions and one transverse incision connecting the origins of the parallel incisions were made. The flap, thus formed was raised and remained attached to the animal only at the caudal end. This model produced severe necrosis at the cranial end of the flap, rapid revascularization at the caudal end and subsequent reversal of ischemia.

Hammond, et al. (1993) *Plast. Reconstr. Surg.* 91:316–321 developed another model based on the monopedicle flap of McFarlane, et al. Hammond, et al. sutured the monopedicle flap atop the closed normal skin on the back of the animal. This technique inhibited revascularization of the flap from the underlying tissue but the flap lacked a closed structure. The Hammond, et al. model was thus prone to infection, drying and necrosis. Moreover, the wounds made in the Hammond, et al. flap model lacked the underlying vasculature and thus failed to simulate the clinical situation.

Shultz, et al. (1998) *Keystone Symposia*, January 10–15 developed a Gortex™ sheet implant model. By this model a Gortex™ sheet was implanted beneath the flap (created as described by Schwartz, et al. infra) and above the underlying structures. Unfortunately, the sheet acted as a barrier to the wound healing process rendering any conclusions regarding the impact of ischemia or tissue repair tenuous at best.

At the present time there are no reproducible models of controlled chronic cutaneous tissue ischemia available for the purpose of assessing wound healing therapeutics. In addition to the recognized difficulty encountered in creating reproducible levels of ischemia in tissue, there is another problem related to the anatomical differences between rodent and human skin which make ischemia models difficult to create—wound contraction.

Skin in lower mammals, like rodents, contains a subcutaneous layer of muscle, called *Panniculus carnosus*. The rodent skin is loosely attached to underlying structures which accounts for its characteristic mobility. The initial mechanism for cutaneous wound repair in these species is contraction. Humans lack the rodents' subcutaneous muscular layer except for some areas in the neck and upper chest. The skin in humans is firmly attached to the underlying structures by means of subcutaneous ligaments and adipose tissue. This is especially true of the areas where ischemic ulcer wounds usually develop such as on the feet. In these areas the skin is attached to the fascia and bone, causing the skin to resist contraction.

The present invention provides the skilled artisan with an animal model of cutaneous ischemia having minimal tissue contraction. Minimal tissue contraction, simulating the human condition, is accomplished for the first time, in connection with the present invention by an implanted stent. Minimal tissue contraction permits granulation tissue formation and epithelialization to be monitored in respect of the healing process of ischemic wounds.

The model employed effectively simulates the frequent clinical situation when ischemic wounds occur i.e. in areas anatomically challenged for skin mobility and contraction, such as feet. The closed structure of the ischemic flap of the present invention resists infection and drying, thus creating a viable zone of suboptimal cutaneous perfusion. With the present invention, the practitioner can now inexpensively and reproducibly create a model of cutaneous ischemia which can provide crucial information about the efficacy of applied wound healing therapeutic agents.

SUMMARY OF THE INVENTION

The present invention is directed to the assessment of ischemic wound therapeutics. By assessment is meant in vivo standardized testing of the effects of wound healing therapeutics applied to an animal model of cutaneous ischemia. Such cutaneous ischemia is inexpensively and reproducibly created for the first time in accordance with the present invention by means of a surgically created cutaneous flap on the back of a laboratory animal. The cutaneous flap has a mechanical framework implanted thereunder for stability. In a preferred embodiment the framework is a stent.

In one embodiment of the present invention chronic cutaneous ischemia is created by surgically constructing a tissue flap on the back of an animal. In a preferred embodiment the animal is a rodent. In a most preferred embodiment the rodent is a rat.

In another embodiment the cutaneous flap has a length to width ratio of about 2.5 to 1. In a preferred embodiment the length to width ratio is 2.5 to 1.

In another embodiment a mechanical framework is implanted under the cutaneous flap and the edges of the flap are brought together and closed around the framework.

In still another embodiment one or more wounds are inflicted on the cutaneous flap.

In a further embodiment wound therapeutic agents are applied to the wound. In a preferred embodiment the wound therapeutic agent is applied from zero to about sixty days post-wounding.

In yet another embodiment the effects of the wound healing therapeutics are conventionally assessed.

Still another embodiment of the present invention is directed to an animal model for assessing ischemic wound healing therapeutics which contains a mechanical framework implanted under a surgically created cutaneous flap.

In another embodiment ischemic conditions are created in the cutaneous flap. In a preferred embodiment ischemic wound conditions are confirmed by the presence of less than about 5% contraction, less than about 0.5 mm epithelialization and less than about 0.3 mm granulation tissue formation.

BRIEF DESCRIPTION OF THE FIGURES

The patent or application file contains at least one drawing executed in color. Copies of this patent or patent application with color drawing(s) will be provided by the office upon request and payment of the necessary fee.

DETAILED DESCRIPTION OF THE INVENTION

Figure 1:
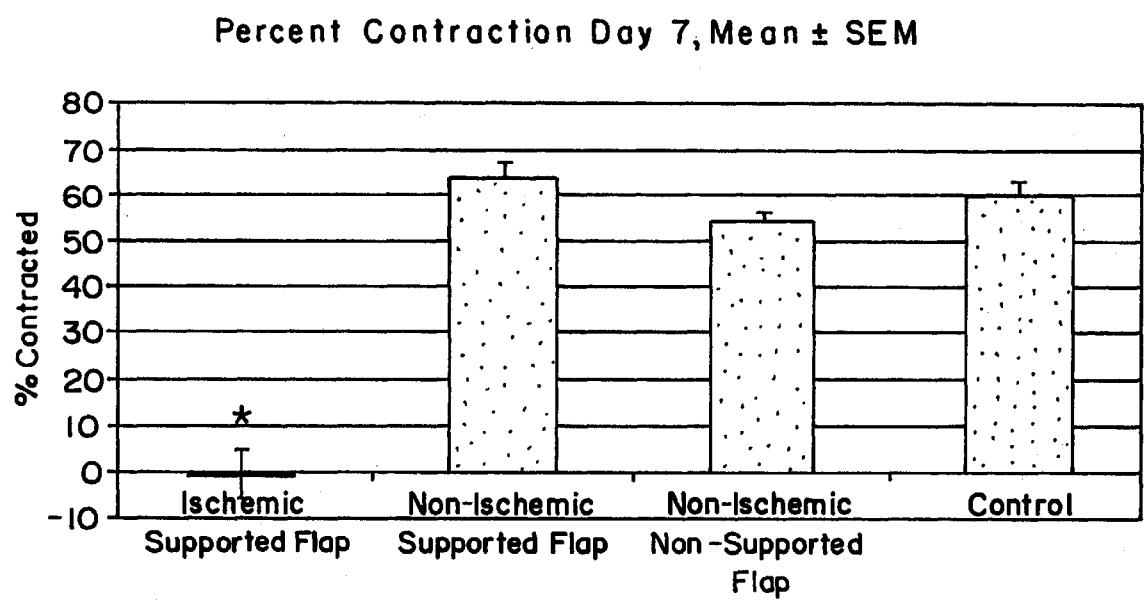
FIG. 1 illustrates that the ischemic supported flap demonstrated significantly delayed wound contraction in relation to all other study groups.

The present invention provides a method for assessing ischemic wound healing therapeutics. The present invention also provides a model of cutaneous ischemia for wound healing assessment. In accordance with the present invention a wound is any damage leading to a break in the continuity of the skin.

Ischemic tissue wounds are characterized in accordance with the present invention as resulting from hypoperfusion caused by arterial occlusion, veneous obstruction and/or impaired microcirculation. By "microcirculation" is meant blood flow or perfusion at the level of the capillary bed. In ischemic tissue at the microcirculatory level, the capillary networks are congested with non-clotted blood and distended vessels. Blood flow bypasses the capillary bed in favor of areas of less resistance, causing poor tissue nutrition. At the macro level, ischemic tissue is cold, grayish in color and rigid.

Ischemic tissue wounds are characterized in accordance with the present invention by several parameters including necrosis development, decreased contraction, decreased epithelialization and decreased granulation tissue formulation relative to non-ischemic tissue wounds.

Necrosis is localized tissue death, generally resulting from continued ischemia.

Contraction refers to a normal mechanism for cutaneous wound repair whereby the wound surface area shrinks over time. In accordance with the present invention wound contraction is calculated as a percentage by the formula:

$$\% \text{ contraction} = [\text{Area(Day } O) - \text{Area(Day } X)/\text{Day } O] \times 100$$

Epithelialization refers to the distance of epithelial cell migration during wound healing. Specifically, during epithelialization, the wound is covered by epithelial cells and scar tissue and the surface area of the wound decreases.

Granulation tissue formation is another wound healing parameter. During granulation tissue formation, macrophages produce growth factors which attract fibroblasts to the wound and stimulate the production of collagen. During granulation, the wound starts to contract thereby reducing the surface area of the wound. The average thickness of granulation tissue is determined as an average distance between the bottom of the wound and the top of the granulation tissue. This parameter is calculated by dividing the area of the granulation tissue by the wound length.

Ischemic wound healing therapeutics can now be accurately assessed by means of the present animal model and methods detailed herein.

Assessments of ischemic wound healing therapeutics are achieved for the first time with the present invention by:

(a) surgically creating a cutaneous flap on an animal;

(b) implanting a mechanical framework under the flap created in step (a);

(c) closing the flap created in step (a);

(d) inflicting at least one wound on the cutaneous flap created in step (a);

(e) applying at least one therapeutic agent to said wound; and (f) characterizing the effect of the wound healing therapeutic on the wound.

It has also been discovered in accordance with the present invention that closure of a surgically created cutaneous flap having a mechanical framework implanted thereunder creates a model system with essentially no revascularization from surrounding skin. The system also provides protection from drying, infection and other adverse environmental factors. Closure of the cutaneous flap is conventionally achieved by suturing or stapling the edges of the flap together. The mechanical framework serves to restrict contraction of the flap tissue and to avoid intimate contact with underlying tissue by supporting the flap in a position adjacent but remote from the underlying body tissue. The closed cutaneous flap is resistant to e.g. drying, infection and other adverse environmental conditions because the epidermis of the animal creates a natural barrier to such adverse conditions. In addition to tolerance to outside environmental factors, the closed structure of the present invention permits the cutaneous flap to undergo natural remodeling and angiogenesis which leads to formation of collateral vasculature and enhanced viability. Moreover, the implanted mechanical device stabilizes the cutaneous flap preventing kinking of the flap, self-mutilation and damage caused by the experimental animal.

Figure 10A:
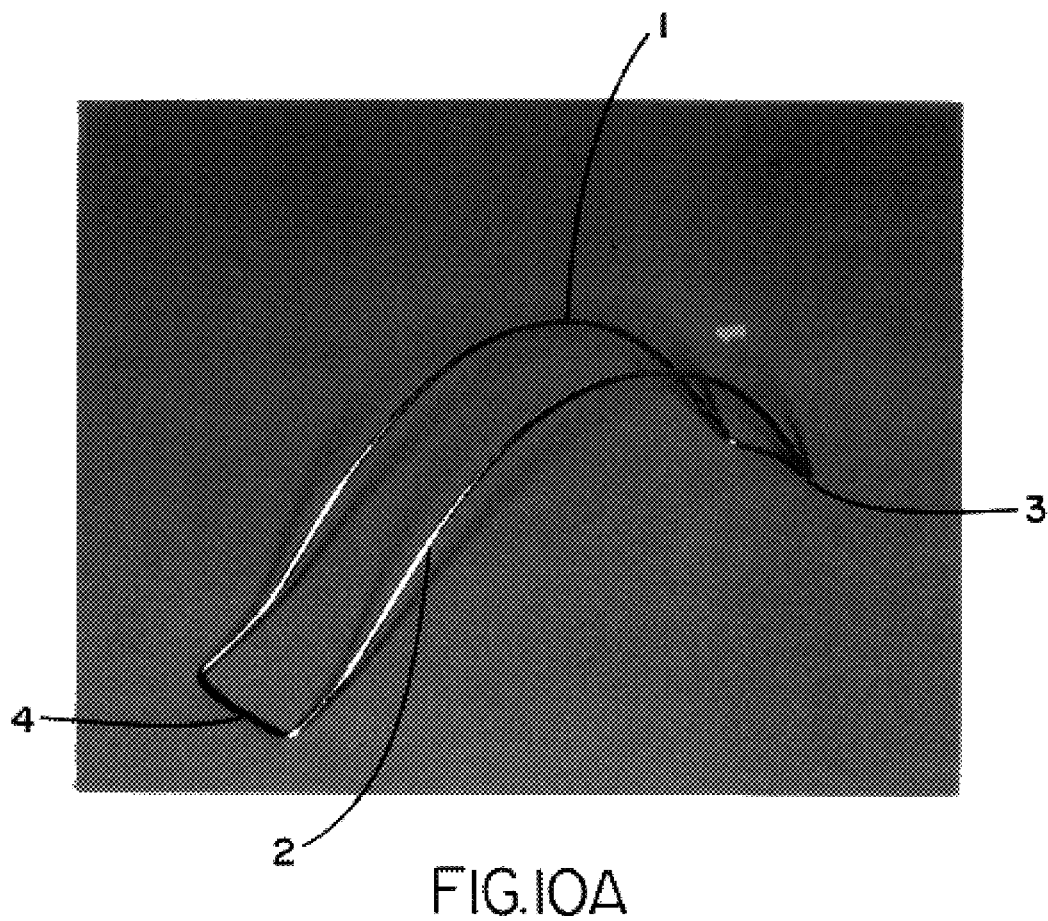
FIG. 10A depicts the mechanical framework having longitudinal distal (1) and proximal (2) branches and transverse spinal (3) and caudal (4) branches.
Figure 10B:
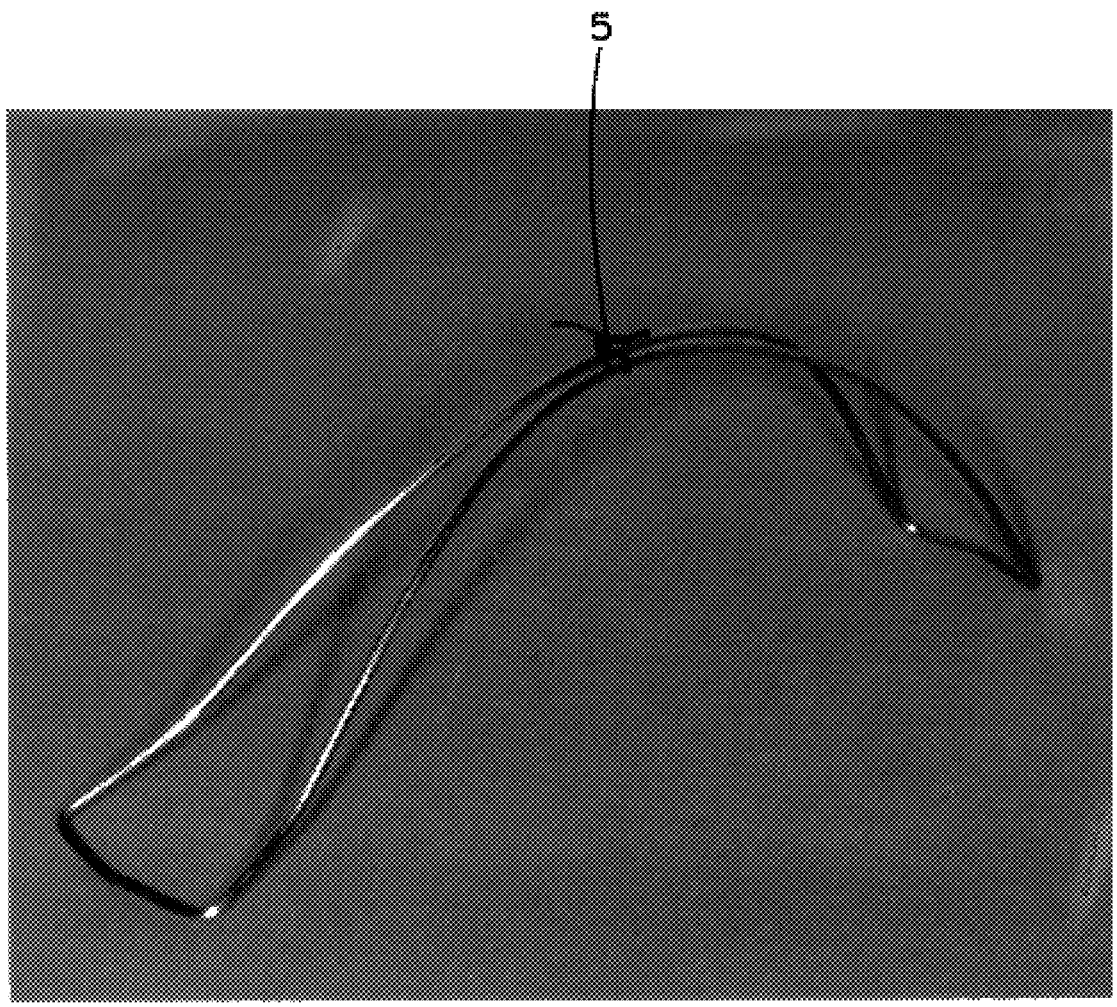
FIG. 10B depicts the framework having a 3/0 prolene suture (5) securing the distal (1) and proximal (2) branches together.

The framework employed by the present invention is preferably of stainless steel construction. However, other physiologically compatible frameworks are contemplated by the present invention including but not limited to biocompatible polymer-based plastic devices and the like. By framework is meant stents, lattices, standoffs and the like which are characterized by their ability to stabilize cutaneous tissue and prevent or inhibit skin contraction. The construction of the device is generally curvilinear and affords an extended dimension typically employed in parallel with a body feature, such as the spine of the animal. The mechanical framework may be, and commonly is, formed or shaped to match the normal body contours in the region of the cutaneous flap. In use, respective caudally and spinally opposed edges of the generally elongate structure (arranged to terminate at or near the cranial and caudal ends of the cutaneous flap) are configured to be seated on the underlying body tissue, thereby forming a raised or elevated bridge over the exposed tissue. The closure is thereafter configured over the bridge and formed by suturing to the surrounding tissue. The branches of the framework of the present invention can be sutured together. Once the suture is removed, the framework automatically returns to its original structure. In accordance with a preferred embodiment of the present invention, the framework is configured into a configuration which approximates the curvature of the spine of the animal (FIG. 10A and FIG. 10B).

In accordance with the present invention the artisan can regulate perfusion values such that ischemic zones are created on the flap when the framework is opened. Also, in accordance with the present invention, blood flow is regulated with simple mechanical devices including, but not limited to clamps and tourniquets. Such devices permit the creation of arterial ischemia and/or veneous stasis along the cutaneous flap on a long-term basis. Perfusion values in normal skin are generally around 20 to about 80 perfusion units. Preferably, perfusion values in the ischemic zones of the flap range from about 2 to about 20 perfusion units.

In accordance with the present invention, perfusion values are measured post-operatively and non-invasively using a Laser Doppler Imager (Moor Instruments, Inc., Wilmington Del.). The instrument allows non-contact, non-invasive scanning of the skin surfaces by a low power laser beam. The moving blood in the microvasculature causes a Doppler shift which is processed to create a color-coded image of blood flow.

According to the present invention, an animal, preferably a rodent and most preferably a rat, is employed to assess the efficacy of wound healing therapeutics. Lower mammals, especially rats possess a subcutaneous layer of muscle called *Panniculus carnosus*. The rodent skin is loosely attached to the underlying structures. Accordingly, the rodent skin is highly mobile and does not readily contract under ischemic wounding conditions. Similarly, in humans, ischemic ulcers develop on areas of skin which are attached to e.g. the fascia and bone, thereby making contraction extremely difficult. One such area is on the feet. One discovery of the present invention is that stabilization of animal skin, preferably rodent and most preferably rat skin with a mechanical device, creates a zone which approximates the human skin condition.

Another discovery of the present invention is that a surgically created cutaneous flap, preferably having a length to width ratio of about 2.5 to 1 can be mechanically stabilized by a mechanical framework. The framework is preferably constructed with an aspect ratio in conformance with the ratio of the length to width of the cutaneous flap typically 2.5 to 1. Preferably the stent is about 10 mm by 150 mm, most preferably 13 mm by 120 mm. Mechanical stabilization of the cutaneous flap permits the creation of controlled and reproducible levels of ischemia in the subsequently wounded tissue by conventional clamps and/or tourniquets and the like.

In accordance with a preferred embodiment of the present invention, the cutaneous flap is prepared longitudinally (e.g. cranially-caudally) such that a mechanical framework is placed subdermally under and into the formed flap. The framework is preferably rectangular shaped having two long ends or branches (distal and proximal) and two short branches. One short branch at the caudal end of the flap is generally straight, approximately 90° relative to the long branches. The short branch at the spinal end of the framework is also generally straight except for a bow or bend in the middle of the branch which conforms with the animals' spine (FIG. 10). The framework is secured to the underlying muscle at the caudal and spinal branches. The distal and proximal branches are sutured together at a mid-point between the spinal and caudal branches. The edges of the cutaneous flap are brought together and conventionally sutured closed over the framework, thereby creating an inverted "U"-shaped flap on the back of the rodent. Once the suture in the middle of the framework is cut, the flap resembles a tube. The system thus created is closed and blood-flow through the flap is artificially decreased by means of clamps and tourniquets, for example. Manipulation of blood flow enables the control of chronic tissue ischemia for wound healing therapeutic agent studies.

Following creation of the cutaneous flap, the animals are wounded, dressed and covered to prevent self-mutilation of the wound. The wounds contemplated by the present invention include, full-thickness and partial thickness excisional, incisional, burn and infectious wounds. Significantly, the inventors have discovered that as perfusion decrease through the flap, wound contraction, epithelialization and granulation tissue formation all decrease in relation to decreased perfusion. In accordance with the present invention ischemic wounds preferably exhibit less than about 5% contraction; less than about 0.5 mm epithelialization and less than about 0.3 mm granulation tissue formation.

Subsequently, the wounds may be treated by one or more therapeutic agents which the skilled artisan desires to evaluate. The evaluation process is understood to include the empirical assessments of various dosages of therapeutics which the skilled artisan understands or expects to be useful for healing chronic ischemic wounds. Such therapeutic agents include, but are not limited to, hydrogels, compression bandages, unaboots, foam dressings, hydrocolloids, alginate dressings, debriding agents, appropriate antibiotics, platelet derived growth factor (PDGF) and other growth factors.

According to the present invention, the skilled artisan can now conveniently assess the efficacy of many different types of ischemic wound healing therapeutics using a safe, inexpensive and highly reproducible method. The present method eliminates the need to monitor chronic wound healing therapeutics in a human population.

In another embodiment, the present invention also provides a reproducible model of cutaneous ischemia for wound healing therapeutic assessment. The model contemplated by the present invention may be prepared in accordance with the methodology detailed and exemplified herein. The model of the present invention is used to assess the efficacy of therapeutics designed for treating full thickness and partial thickness excisional, incisional, burn and infectious wounds under conditions of acute and chronic compromised cutaneous perfusion.

In one embodiment the animal model of cutaneous ischemia is prepared by surgically creating a cutaneous flap in a length to width ratio of 2.5 to 1 on the back of a rat. Preferably, the flap is 10 cm by 4 cm. A framework device is inserted and secured to underlying muscle. The flap is closed over the device and the incision on the back of the animal is closed. The flap is subsequently wounded.

In another embodiment several parameters are measured to confirm the presence of ischemic wounds on the cutaneous flap. In a preferred embodiment the wound exhibits less than about 5% contraction. In another preferred embodiment the wound exhibits less than about 0.5 mm epithelialization. In still another preferred embodiment the wound exhibits less than about 0.3 mm granulation tissue formation.

The following examples are intended to further illustrate the invention.

EXAMPLE 1

Forty Sprague-Dawley rats weighing approximately 350 grams (Taconic Laboratories, Germantown, N.Y.) were anesthetized by intraperitoneal injection of ketamine (Fort Dodge Laboratories, Ft. Doge, Iowa) (56 mg/kg) and xylazine (Fermenta Laboratories, Mo.) (6 mg/kg) mixture. The animal husbandry and environmental conditions were in conformance with the specifications of current Johnson & Johnson Consumer Products Worldwide Standard Operating Procedures, which are based on the "Guide for the Care and Use of Laboratory Animals", NIH Publication No. 85-23. The rats were housed in cages (one animal per cage, with a minimum floor area of 50 sq. in./animal) and given an identification on the base of the tail using water resistant permanent marker. A tag was placed on each individual animal cage listing the animal number, species/strain, surgical date, surgical technique, duration of the experiment and date of euthanasia. Animal rooms were maintained at the range of 40 to 70% relative humidity and 18 to 26° C. (64.4 to 78.8° F.). Animals were fed with a standard rat chow ad libitum. Water was also available ad libitum. A daily light-:dark cycle of 12:12 hours was adopted.

Out of 40 animals used for the study, 10 underwent surgical ischemic flap formation (ischemic supported flap), 10 were used as controls with a non-ischemic flap created by an implanted framework non-ischemic supported flap), 10 underwent non-ischemic flap formation without a framework (non-ischemic non-supported flap) and 10 were used as non-operated (normal) controls.

EXAMPLE 2

Surgical Procedures
Ischemic Supported Flap

The skin was cut down to the *Panniculus carnosus* on the back of each animal. Careful hemostasis was achieved by tamponade. The incision originated 2 cm below the base of the skull. A single, bipedicle flap was created by raising the skin between two 10 cm long incisions, placed 2 cm to each side of the vertebra (creating a 10×4 cm bipedicle flap). The subcutaneous tissue was bluntly dissected, preserving the base at the iliac crest and the tip at the scapula. A framework, formed from 18–22 G stainless steel Cerciage wire (J. A. Webster Inc., Sterling, Mass.) was placed subdermally into the newly formed flap to create mechanical stabilization. The frame was formed using standard wire bending kit (J. A. Webster Inc., Sterling, Ha Mass.) and sterilized by autoclaving prior to the implantation. The standardized design of the frame allowed development of reproducible amount of force along the back of the rats and prevented cutaneous contraction. The distal and proximal branches of the stent were brought together and secured with 3/0 prolene suture (Ethicon Inc., Somerville, N.J.) at approximately the midpoint between the spinal and caudal ends of the frame (FIG. 10A and FIG. 10B). The cranial and caudal ends of the framework were secured to the underlying muscle with 3/0 Prolene sutures. The edges of the flap itself were brought together and closed using surgical skin staples, resembling a tube shape. The two longitudinal incisions on the back of the animal which were not raised were brought together and also closed using sutures and/or wound clips (Ethicon Inc., Somerville, N.J.) (FIG. 5).

Non-Ischemic Supported Flap (Sham Control)

A distance of 10 cm was measured along the spine of the animal, starting 2 cm below the base of the skull. Subsequently two lines, parallel to the spine were drawn at the distance of 2 cm from the spine on each side of the animal. The marking resembled that for the ischemic supported flap model. Two longitudinal incisions of 1 cm each were made at full thickness of the skin both above and below the ends of the central marking line. The skin between these two incisions was bluntly separated from the underlying structures by means of a hemostatic forceps. As during the construction of the ischemic supported flap, the distal and proximal branches of the framework were brought together and secured with 3/0 prolene suture. The framework was later introduced into the preformed space and secured to the underlying muscle by 3/0 prolene sutures. The skin around the framework was closed using mattress sutures along the lateral lines, forming a flap (FIG. 6).

Non-Ischemic Non-Supported Flap (Operated Control)

The marking at back of the animals was identical to that for the ischemic supported flap model and non-ischemic supported flap model. The skin was closed using mattress sutures along the lateral lines, forming a flap.

Post operative sutures in the ischemic supported flap were covered with RELEASE™ non-adhering dressing (J&J Medical, Arlington, Tex.), contoured to the curvature of the flap. The flap and the animal were wrapped individually with Vetwrap™ elastic dressing which was secured with adhesive tape. Non-ischemic non-supported flaps on control animals were dressed with Vetwrap™ and adhesive tape. Non-ischemic supported flaps were not dressed.

EXAMPLE 3

Measurement of Blood Flow

In the post-operative period, perfusion of the created flap was monitored non-invasively by means of a Laser Doppler Imager (Moor Instruments Inc., Wilmington, Del.). The instrument allowed non-contact, non-invasive scanning of the skin surface by a low power laser beam. The moving blood in the microvasculature caused a Doppler shift which was processed to create a color-coded image of blood flow. Perfusion at each image position was recorded for further analysis. An area of 4×12 centimeters was scanned, which included both ischemic and non-ischemic zones for comparative analysis. The overall length of time for measurements for each animal was approximately 2 minutes.

EXAMPLE 4

Post-Operative Follow-Up and Wounding

At Day 6 after the flaps were formed, the suture connecting two branches of the stent was cut via small puncture access through the skin. This procedure was performed on non-ischemic supported flaps as well. After 7 days of flap formation, one full-thickness excisional wound of 1×1 centimeter in size per flap was created with the #15 scalpel blade. At the same time, wounds were made in the non-ischemic supported flaps, non-ischemic non-supported flaps and controls. The wounds were dressed with 1.5×1.5 cm pieces of RELEASE™ (J&J Medical Inc., Arlington, Tex.) and covered with BIOCLUSIVE™ (J&J Medical Inc., Arlington, Tex.) transparent dressing and Vetwrap™ (3M Inc.), to prevent self-mutilation of the wound sites. The wounds were not treated. Dressings were changed at 1, 2, 3, 4 and 7 days post wounding.

Digital images of the wounds were taken at 0, 2, 4 and 7 days post wounding time-points throughout the study using E2N Digital Still Camera (Nikon Inc., Japan). The animals were euthanized with inhalation of carbon dioxide. After identifying that the animals were dead, the wounds and surrounding tissue were removed from the animal and dissected in two parts. The cranial part was immediately placed in 10% buffered formalin for histology. The caudal part was snap frozen in liquid nitrogen.

EXAMPLE 5

Histological Processing

After 24 hours exposure in 10% Neutral Buffered Formalin the samples were processed by conventional methods and embedded in paraffin. Subsequently, the blocks were sectioned at 5 $\mu$m and stained in Hematoxyline and Eosin and Masson Trichrome.

Contraction Rate Measurement

In vivo capturing of the wound images was carried out via Nikon/Fujix E-2N Digital Camera, 105 Nikon Macro AF lens (Nikon, Japan) at Days 0, 4 and 7 post-wounding. A fixed focus system and strict positioning in the camera plane perpendicular to that of the wound allowed complete elimination of errors in wound size, related to image capturing. In addition to that, a calibration ruler was captured in every image. Images were directly downloaded into the memory Micron Millenia Pentium II computer (Micron Electronics Inc., Nampa, Id.) in true color, 24 bits per pixel mode. Subsequently, areas of the wounds were measured by tracing the wound margins and automatically calculating the surface areas. The percentage of contraction was calculated using the following values.

$$\% \text{ of contraction}=[\text{Area}(\text{Day } O)-\text{Area}(\text{Day } X)/\text{Day })]*100$$

Histological Assessment

Images from the light microscope Nikon Microphot FXA (Nikon, Japan) were captured into the computer memory using a VI-470 CCD camera (Optronics Engineering, Goleta, Calif.) and Imagraph Chroma frame grabber board and subsequently analyzed using Image Pro 1.3 Image analysis software (Media Cybernetics, Inc.). Since the specimens were larger than the area covered by one field, motorized controllable stage by Prior Inc. (Cambridge, United Kingdom) was used to map the images of the separate fields to ensure accuracy. Spatial calibration was performed by capturing the image of the micrometer slide and applying the calibration feature of the imaging software. Separate calibration was performed for each magnification using in microscopy (10×, 20×, 40×, 100× and 400×).

Distance of the Epithelial Tongue Migration (Epithelialization)

The distance of the epithelial tongue migration was measured under 40× magnification on H&E stained specimen. A line was drawn along the basal membrane of the epithelial tongue and the length was calculated automatically by the software program. The exact location of the end of the epithelial tongue was visualized via higher magnification (100×). The sum of the two lengths of trace lines (left and right wound margin) was calculated. The distance of the epithelial tongue migration was expressed in mm.

Granulation Tissue Formation

Granulation tissue formation parameters were evaluated on Masson's Trichrome stained specimens using 20× magnification. Use of the automatic slide scanning system allowed capturing of the image of the entire slide.

The average thickness of the whole granulation tissue was an average distance between the bottom of the wound and the top of the granulation tissue. It was calculated by dividing the area of the granulation tissue by the wound length. This parameter was expressed in mm.

EXAMPLE 6

Statistical Analysis

One-way ANOVA was performed on continuous data, followed by Tukey-Kramer or Student-Newman-Keuis test for multiple comparison when significance was detected among groups. A value of $P<0.05$ was used as the level of significance. Sperman correlation analysis was conducted to assess correlation between the parameters. Significance limits for r was determined by sample size.

EXAMPLE 7

Flap Perfusion

Figure 4:
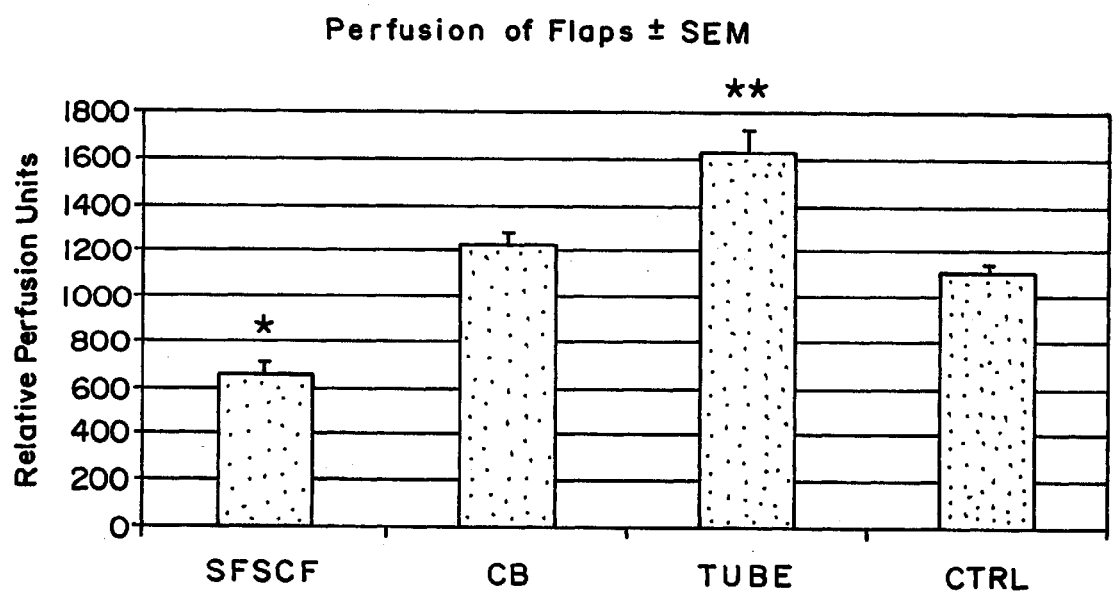
FIG. 4 illustrates that the ischemic supported flap demonstrated significantly decreased perfusion in relation to all other study groups.
Figure 5A:
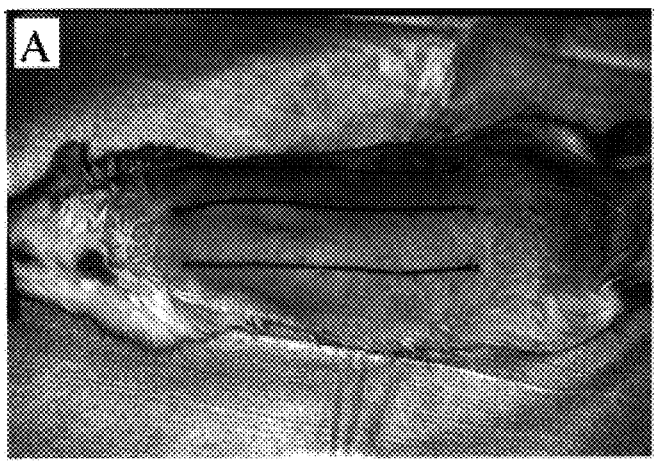
FIG. 5 illustrates the preparation of an ischemic rat model.
A. The back of the animal was marked with two parallel lines 4 cm apart. The middle line defined the spine.
B. Two incisions were made and the flap was raised after blunt dissection. The framework was inserted and secured to the underlying muscle.
C. The flap was closed over the framework.
D. The incision on the back of the animal was closed.
E. The flap was completed.
F. The flap was dressed using RELEASE™, Vetwrap™ and adhesive tape.
Figure 5B:
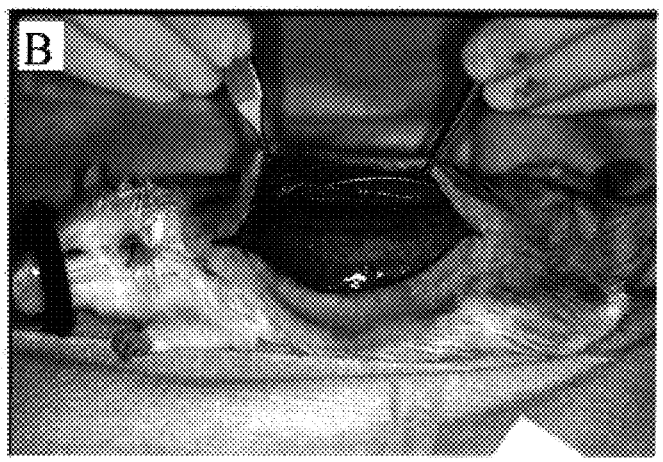
Figure 5C:
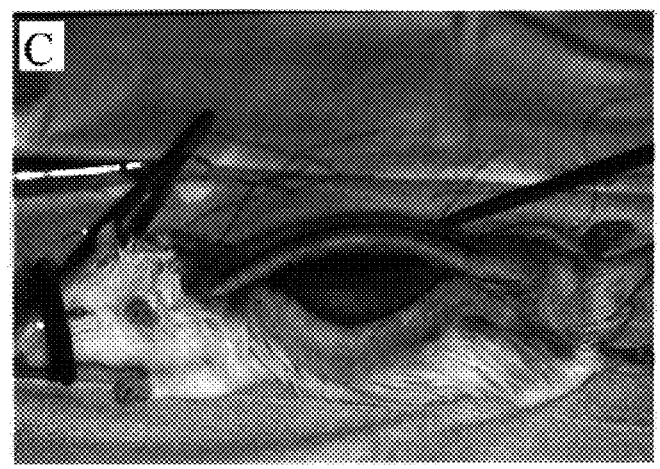
Figure 5D:
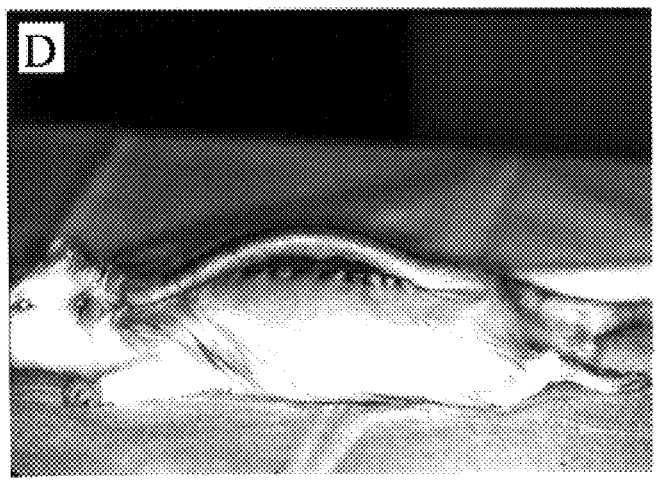
Figure 5E:
Figure 5F:
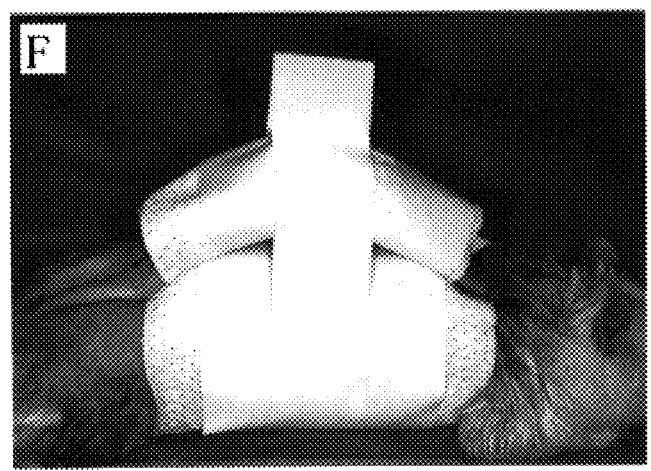
Figure 6A:
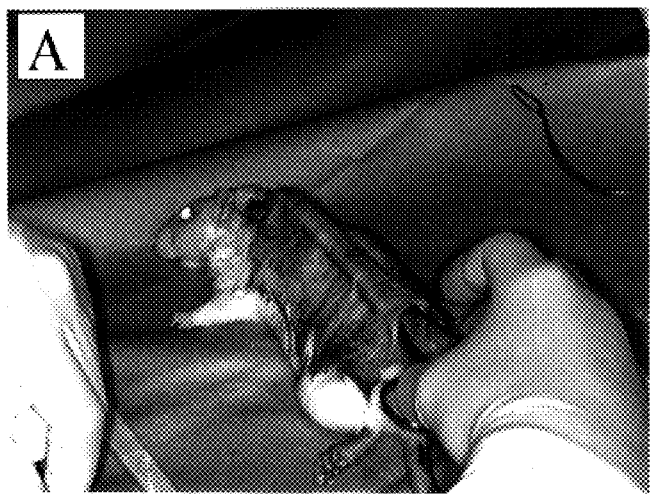
FIG. 6 illustrates the preparation of a non-ischemic rat model.
A. A tunnel was made in the subcutaneous tissue, using a hemostatic clamp.
B. The framework was inserted subcutaneously.
C. The framework was secured to the underlying muscle via separate cranial and caudal incisions.
D. Layers of skin were approximated over the framework using mattress sutures.
E. Formation of the framework tube was completed. Access incisions were closed with wound clips.
F. Final view of the complete model.
Figure 6B:
Figure 6C:
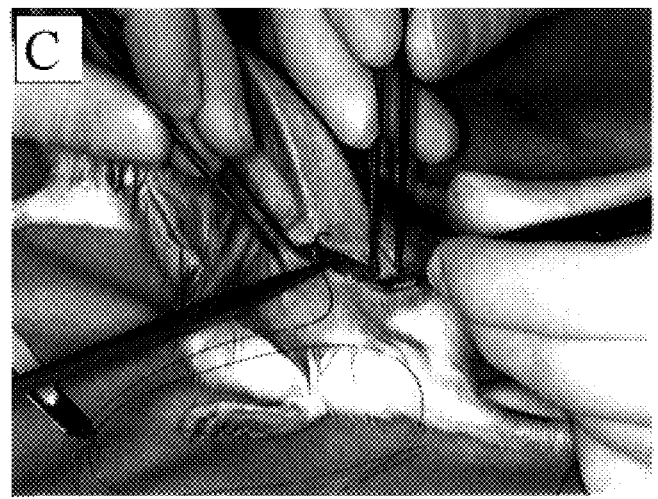
Figure 6D:
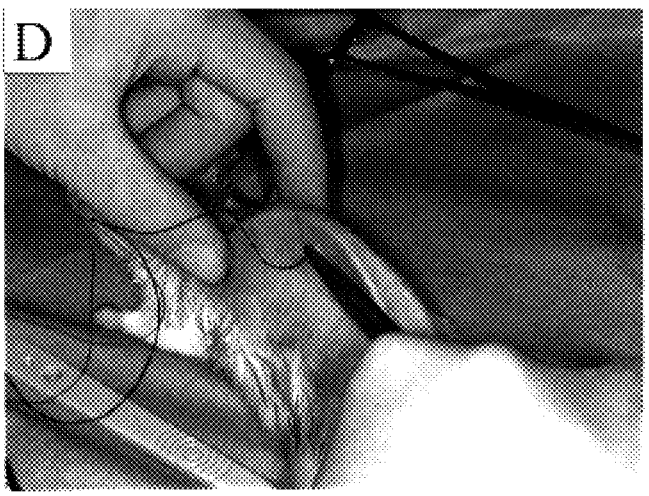
Figure 6E:
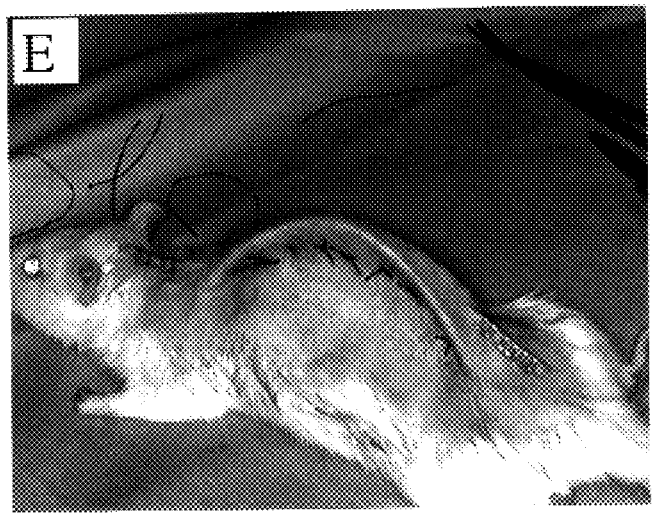
Figure 6F:
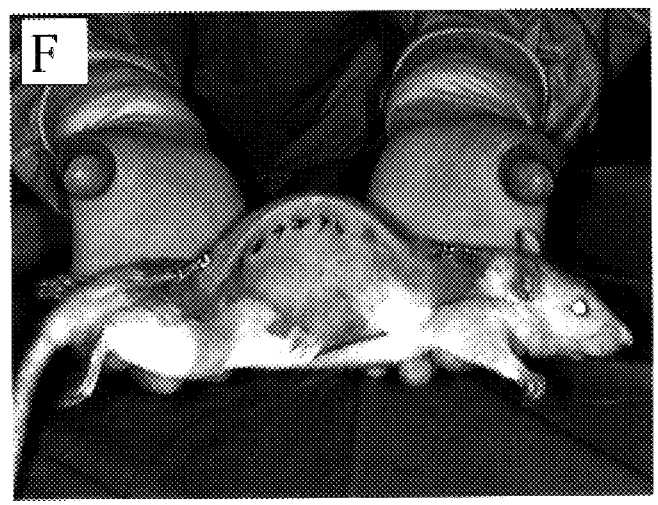
Figure 7A:
FIG. 7 illustrates granulation tissue in the full thickness excisional wounds.
A. A wound made on the ischemic supported flap. Note virtually complete absence of the granulation tissue.
B. A wound made on the non-ischemic supported flap.
C. A wound made on the non-ischemic non-supported flap.
D. A wound made on the control animal.
Figure 7B:
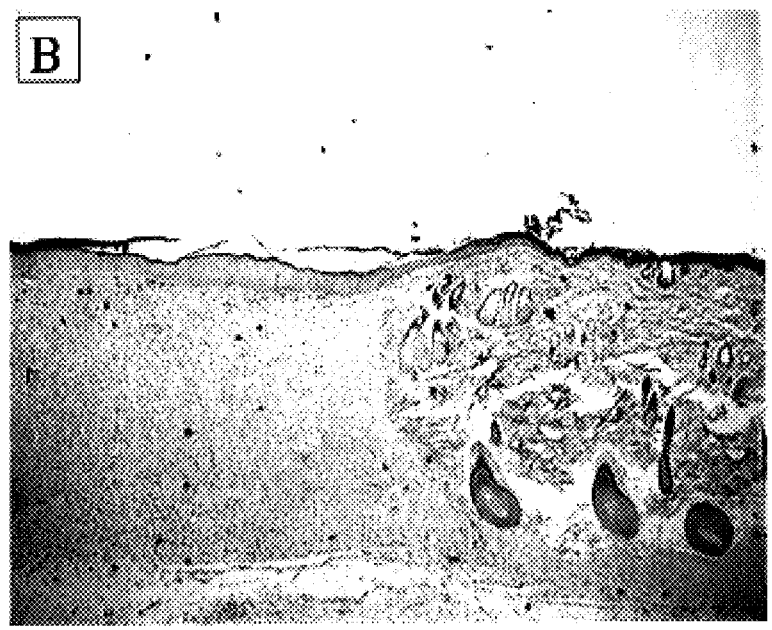
Figure 7C:
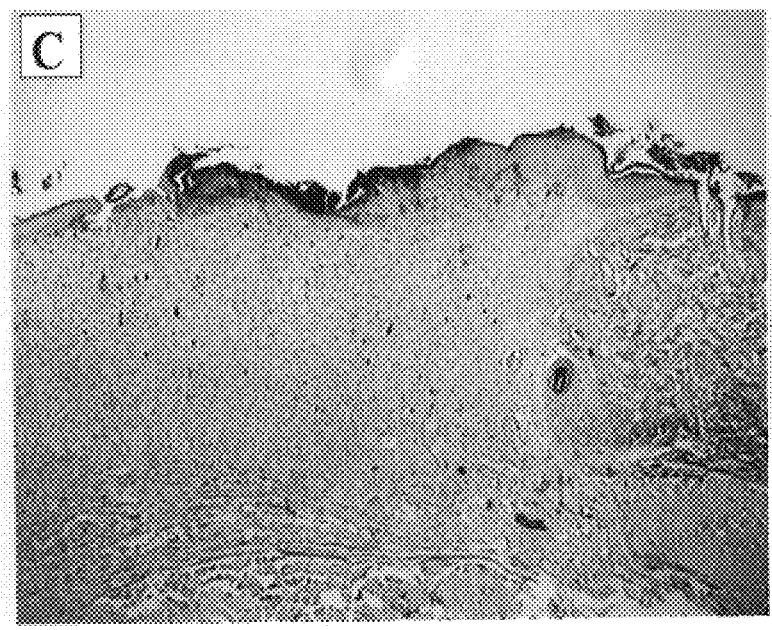
Figure 7D:
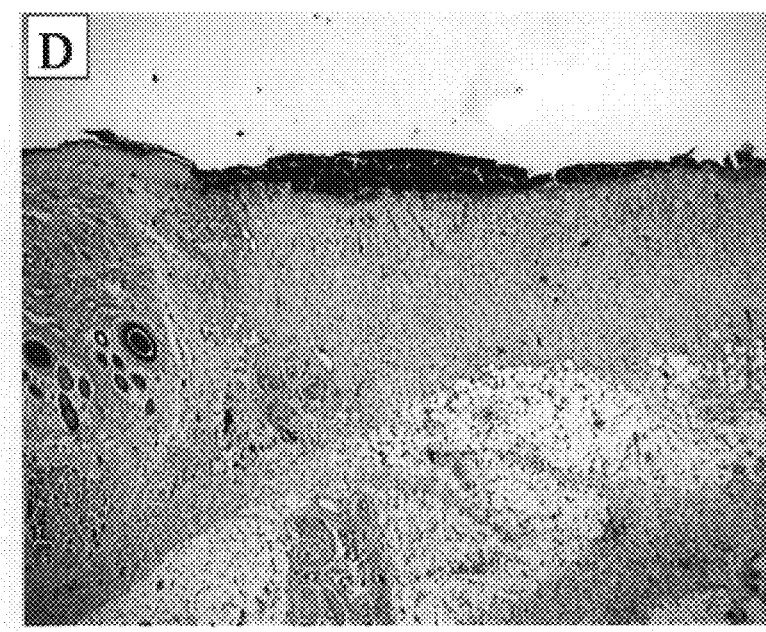
Figure 8A:
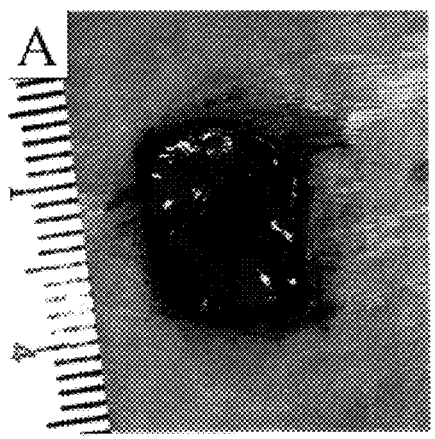
FIG. 8 illustrates wounds at different evaluation time points.
A,B,C. Wounds created on the control animal, Days 0, 4 and 7, respectively.
D,E,F. Wounds created on the non-ischemic non-supported flap, Days 0, 4 and 7, respectively.
G,H,I. Wounds created on the non-ischemic supported flap, Days 0, 4 and 7, respectively.
J,K,L. Wounds created on the ischemic supported flap. Days 0, 4 and 7, respectively.
Note a significant delay in the healing of the ischemic wound.
Figure 8B:
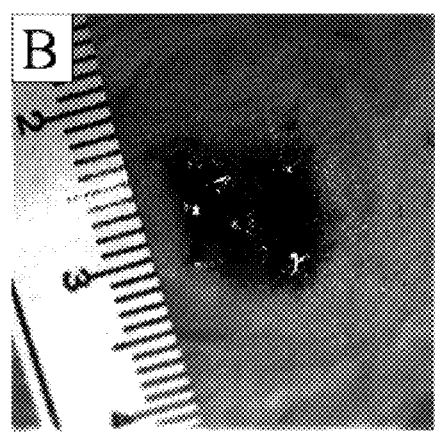
Figure 8C:
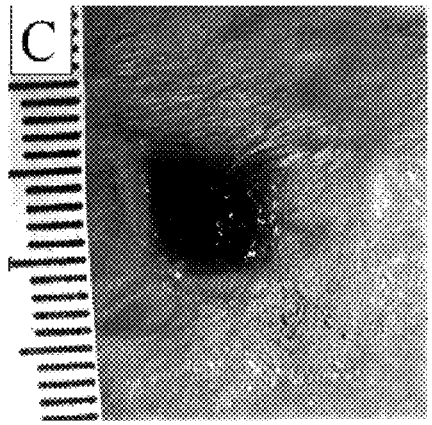
Figure 8D:
Figure 8E:
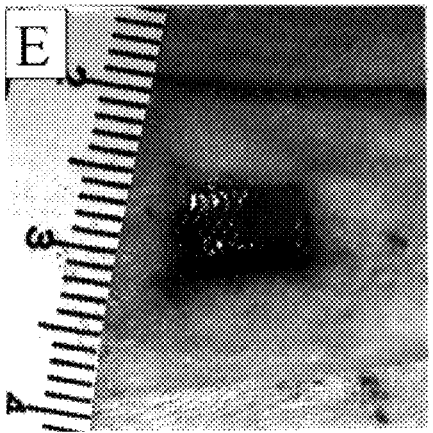
Figure 8F:
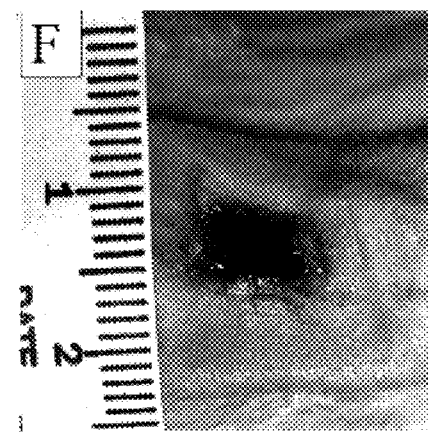
Figure 8G:
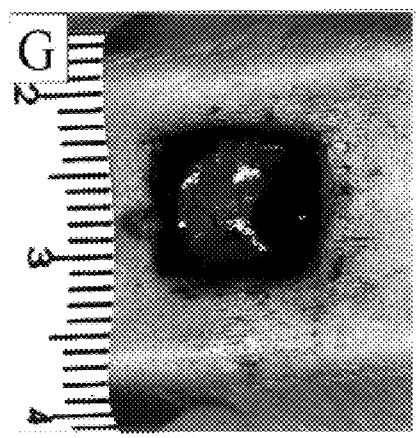
Figure 8H:
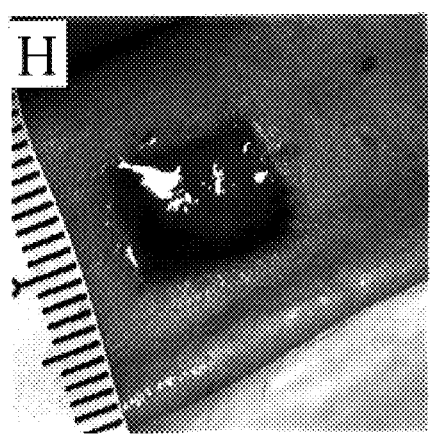
Figure 8I:
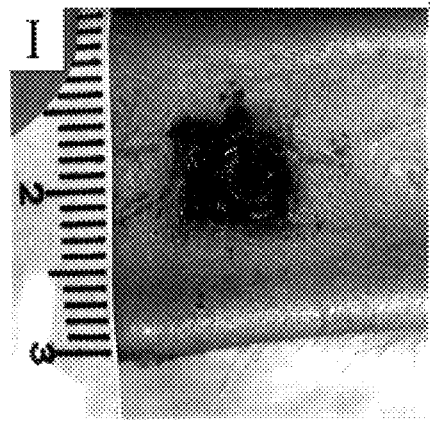
Figure 8J:
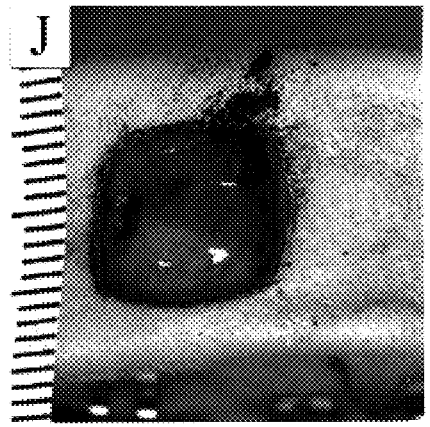
Figure 8K:
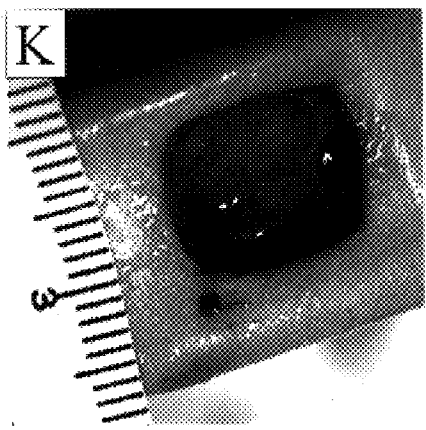
Figure 8L:
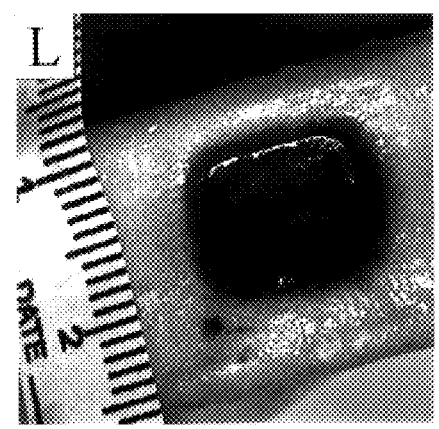

Flap perfusion was measured at seven days post flap formation at the day of wounding. The ischemic supported flap model had significantly lower perfusion than all other groups, and the non-ischemic non-supported flap had significantly higher perfusion than all the other groups (Tukey-Kramer HSD). There was no significant difference between non-ischemic supported flap and control groups (Tukey-Kramer HSD) (FIG. 4).

Contraction

At Day 4, the ischemic supported flap model was significantly less contracted than all other groups (Tukey-Kramer HSD). There was no significant difference between non-ischemic supported flap, non-ischemic non-supported flap, and control groups in wound contraction at Day 4 (Tukey-Kramer HSD). On Day 7, the ischemic supported flap was significantly different from all other groups (Tukey-Kramer HSD) and no difference between non-ischemic supported flap, non-ischemic non-supported flap and control groups was observed (FIGS. 1 and 8).

EXAMPLE 8

Histopathological Examination

Figure 9A:
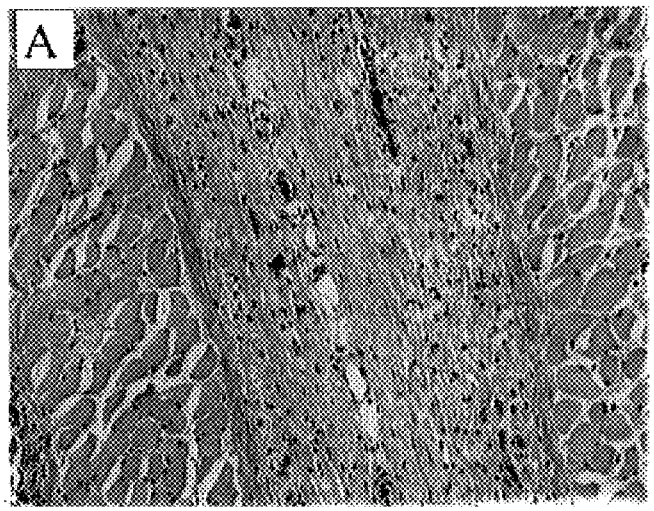
FIG. 9 depicts histopathological assessment of the ischemic supported flaps.
A. Connective tissue formation between the layers of the folded skin in the ischemic supported flap.
B. Fibrotic capsule formation around the stent in the ischemic supported flap.
C. Congested blood vessels in the ischemic supported flap.
Figure 9B:
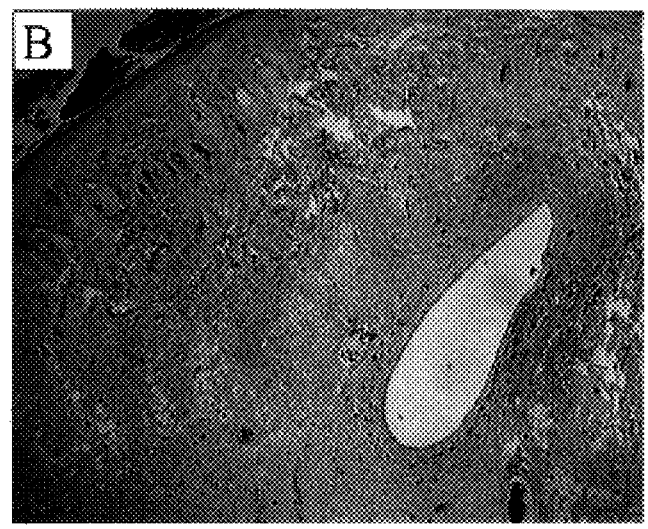
Figure 9C:
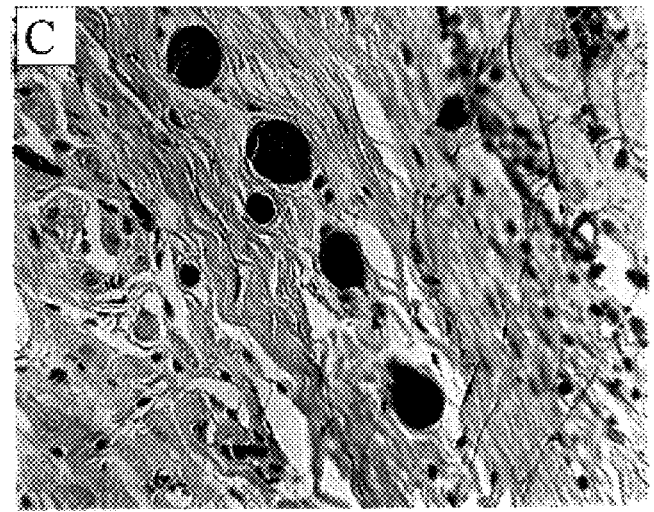

Microscopic examination of the ischemic supported flap revealed the presence of microvascular disturbances related to blood vessel congestion and obliteration. Formation of the connective tissue containing newly formed blood vessels between the folded layers of flap was observed. The framework was found to be surrounded by a thin capsule without signs of excessive inflammatory response. Areas of epidermal necrosis was occasionally observed throughout the samples. These lesions were noted to be healing by the re-epithelialization. Cells of the skin appendages such as hair follicles on sebaceous glands demonstrated occasional signs of cytoplasmic swelling and karyopyknosis. The microscopic examination of the skin of non-ischemic supported flaps, non-ischemic non-supported flaps and control animals was unremarkable (FIG. 9).

Epithelialization

Figure 3:
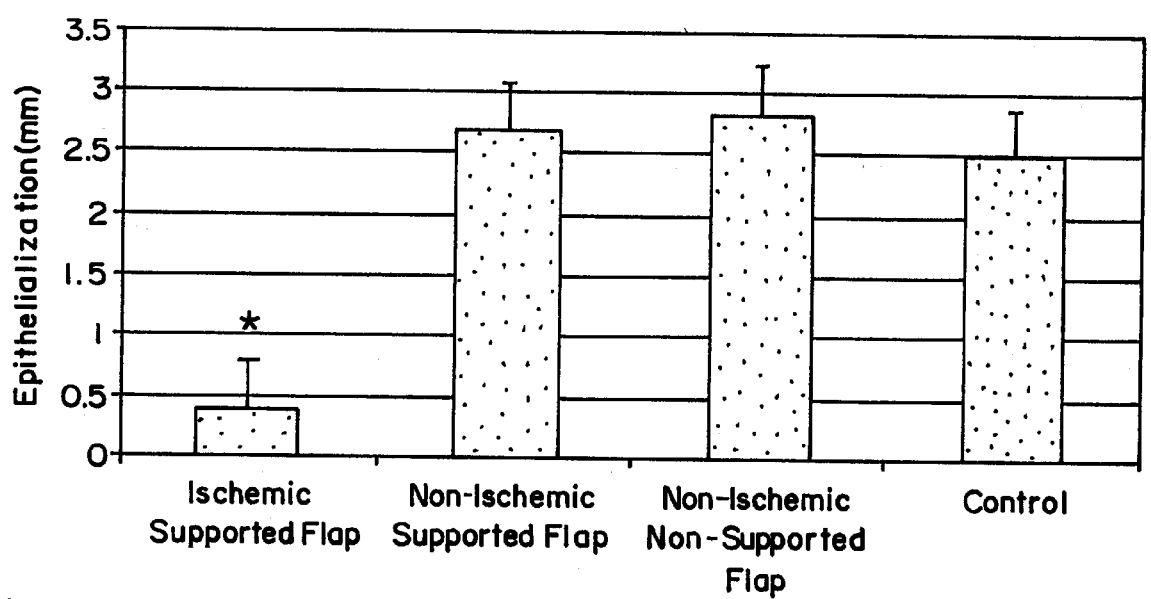
FIG. 3 illustrates that the ischemic supported flap demonstrated significantly decreased distance of epithelialization in relation to all other study groups.

The ischemic supported flap model was found to have significantly less re-epithelialization than all the other groups (Tukey-Kramer HSD). There was no significant difference among the other groups (FIG. 3).

Granulation Tissue Thickness

Figure 2:
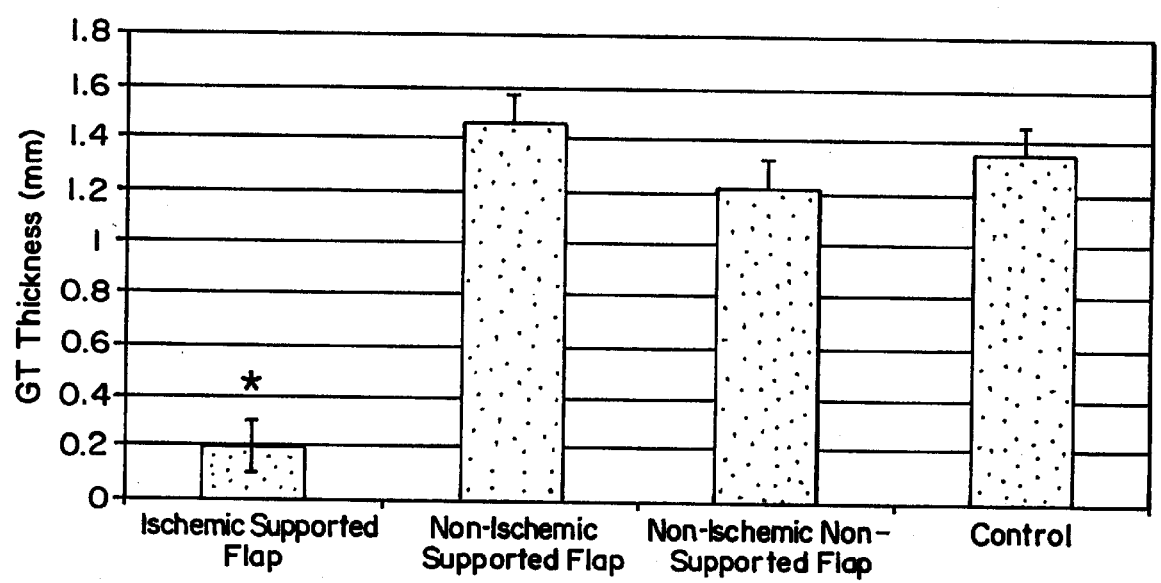
FIG. 2 illustrates that the ischemic supported flap demonstrated significantly decreased thickness of granulation tissue in relation to all other study groups.

The ischemic supported flap model had significantly less granulation tissue formation in the wound bed than all the other groups (Tukey-Kramer HSD). There was no significant difference among the other groups (FIG. 7). FIG. 2 depicts granulation tissue thickness by group.

Correlation

Perfusion was found to be significantly correlated to contraction, epithelialization and granulation tissue thickness. The correlation coefficient values were 0.627 for Day 7 contraction, 0.603 for epithelialization and 0.600 for granulation tissue thickness with respect to flap perfusion. When the perfusion decreased, so did all other wound parameters.

We claim:

1. A method for assessing ischemic wound healing therapeutics comprising:
   (a) surgically creating a dorsal cutaneous flap on an animal;
   (b) implanting a mechanical framework under said flap;
   (c) closing said cutaneous flap;
   (d) inflicting at least one wound on said cutaneous flap;
   (e) applying at least one therapeutic agent to said wound; and
   (f) characterizing the effect of said wound healing therapeutic on said wound.

2. The method of claim 1 wherein said animal is a rodent.

3. The method of claim 2 wherein said rodent is a rat.

4. The method of claim 1 wherein said cutaneous flap has a length to width ratio of 2.5 to 1.

5. The method of claim 1 wherein said framework comprises stainless steel.

6. The method of claim 1 wherein said wound healing is characterized by contraction, epithelialization and granulation tissue formation.

7. The method of claim 1 wherein said therapeutic agent is applied about zero to about sixty days after said wound is inflicted.

8. A model of cutaneous ischemia for wound healing therapeutic agent assessment comprising an animal having a framework implanted under a surgically created doral cutaneous flap.

9. The model of claim 8 wherein said cutaneous flap has a length to width ratio of about 2.5 to 1.

10. The model of claim 8 wherein said animal is a rodent.

11. The model of claim 10 wherein said rodent is a rat.

12. The model of claim 8 wherein said cutaneous ischemic flap is inflicted with at least one wound.

13. The model of claim 12 wherein said wound exhibits less than about 5% contraction.

14. The model of claim 12 wherein said wound exhibits less than about 0.5 mm epithelialization.

15. The model of claim 12 wherein said wound exhibits less than about 0.3 mm granulation tissue formation.

* * * * *

UNITED STATES PATENT AND TRADEMARK OFFICE
CERTIFICATE OF CORRECTION

PATENT NO.   : 6,250,306 B1                                                       Page 1 of 1
DATED        : June 26, 2001
INVENTOR(S)  : Gritsus et al.

It is certified that error appears in the above-identified patent and that said Letters Patent is hereby corrected as shown below:

<u>Column 12,</u>
Line 46, "created doral" should read -- created dorsal --.

Signed and Sealed this

Sixteenth Day of September, 2003

JAMES E. ROGAN
*Director of the United States Patent and Trademark Office*